United States Patent [19]

Straka, Jr.

[11] Patent Number: 5,645,063
[45] Date of Patent: Jul. 8, 1997

[54] SKIN ELECTRODE HAVING MULTIPLE CONDUCTIVE CENTER MEMBERS

[75] Inventor: Lawrence J. Straka, Jr., Issaquah, Wash.

[73] Assignee: Quinton Instrument Company, Bothell, Wash.

[21] Appl. No.: 464,040

[22] Filed: Jun. 5, 1995

[51] Int. Cl.$^6$ ............................................. A61B 5/0416
[52] U.S. Cl. ................................................... 128/641
[58] Field of Search ................................. 128/635–641

[56] References Cited

U.S. PATENT DOCUMENTS

| | | | |
|---|---|---|---|
| Re. 32,724 | 8/1988 | Cartmell | 128/640 |
| 2,621,657 | 12/1952 | Leech | 128/417 |
| 3,882,853 | 5/1975 | Gofman et al. | 128/641 |
| 4,029,086 | 6/1977 | Corasanti | 128/2.06 E |
| 4,155,354 | 5/1979 | Rasmussen | 128/640 |
| 4,257,424 | 3/1981 | Cartmell | 128/641 |
| 4,265,253 | 5/1981 | Abraham | 128/798 |
| 4,270,544 | 6/1981 | Gilden et al. | 128/640 |
| 4,274,419 | 6/1981 | Tam et al. | 128/639 |
| 4,300,575 | 11/1981 | Wilson | 128/798 |
| 4,311,152 | 1/1982 | Modes et al. | 128/641 |
| 4,319,579 | 3/1982 | Cartmell | 128/640 |
| 4,331,153 | 5/1982 | Healy | 128/641 |
| 4,488,557 | 12/1984 | Engel | 128/635 |
| 4,524,087 | 6/1985 | Engel | 427/2 |
| 4,539,996 | 9/1985 | Engel | 128/640 |
| 4,559,950 | 12/1985 | Vaughan et al. | 128/641 |
| 4,595,013 | 6/1986 | Jones et al. | 128/644 |
| 4,635,641 | 1/1987 | Hoffman | 128/641 |
| 4,660,562 | 4/1987 | House, Sr. | 128/641 |
| 4,669,480 | 6/1987 | Hoffman | 128/641 |
| 4,674,511 | 6/1987 | Cartmell | 128/641 |
| 4,679,564 | 7/1987 | Sessions | 128/640 |
| 4,700,710 | 10/1987 | Hoffman | 128/641 |
| 4,706,680 | 11/1987 | Keusch et al. | 128/640 |
| 4,738,263 | 4/1988 | Seebach et al. | 128/640 |
| 4,757,817 | 7/1988 | Healy | 128/641 |
| 4,768,514 | 9/1988 | De Marzo | 128/640 |
| 4,777,954 | 10/1988 | Keusch et al. | 128/640 |
| 4,798,208 | 1/1989 | Faasse, Jr. | 128/640 |
| 4,838,273 | 6/1989 | Cartmell | 128/640 |
| 4,934,383 | 6/1990 | Glumac | 128/798 |
| 5,114,424 | 5/1992 | Hagen et al. | 606/32 |
| 5,458,141 | 10/1995 | Neil | 128/641 |

FOREIGN PATENT DOCUMENTS 2240928  8/1991  United Kingdom .

OTHER PUBLICATIONS

3M Co., "3M Announces the New High Performance Red Dot® Monitoring Electrode" brochure, date unknown, 5 pages.
Ver–Med, "Ver–Med Breathable Electrode" brochure, date unknown, 2 pages.
Ferris Mfg., Co., "Ferris Trace–Itt Pregelled Disposable Pads for the EKG Lab" literature, date unknown, 1 page.
Medtronic Andover Medical, "ClearTrace™ Monitoring Electrode with Adhesive Gel" literature, date unknown, 1 page.

Primary Examiner—Lee S. Cohen
Attorney, Agent, or Firm—Montgomery W. Smith; Richard D. Allison

[57] ABSTRACT

A medical electrode and skin preparation device is adapted to be secured to the skin of a patient and is designed to allow the user to acquire physiological signals for use by a plurality of signal acquisition devices and optionally to also reliably prepare the skin of the patient by abrasion or penetration of the epidermal layer of the skin which is in conductive contact with the conductive member of the electrode assembly. The electrode assembly includes a plurality of post members capable of conducting physiological signals received from the skin of the patient for acquisition, recording and/or analysis by one or more external devices.

17 Claims, 7 Drawing Sheets

SKIN ELECTRODE HAVING MULTIPLE CONDUCTIVE CENTER MEMBERS

FIELD OF THE INVENTION

This invention relates to an improved medical electrode which is particularly useful in research or comparative studies. The medical electrode of the present invention may also be used perform skin preparation in addition to sensing and recording physiological signals from a single signal acquisition location or a plurality of signal acquisition locations which are spaced apart a predetermined distance from each other on the same electrode. In particular, the electrode of the present invention, after application to the skin, is employed to provide consistent sensing and recording of physiological signals for a plurality acquisition devices.

BACKGROUND OF THE INVENTION

In various comparative studies or research applications, it is oftentimes necessary to apply multiple sets of electrodes to compare the performance of acquisition devices or to obtain an extra set of physiological signals which are to be separately processed. The current practice is to apply the second set of electrodes next to the first set of electrodes on the patient or to cut excess portions of the adhesive pad from an electrode so that the signal acquisition portion of each of the electrodes are as close together as possible. Because an electrode receives electrical signals which represent vectors of the electrical signals of the heart, this type of arrangement may introduce an inherent bias or variability into the acquired data. If the electrodes are offset from each other, the signals that are to be compared will be inherently different and will vary slightly based on the spacing of the electrodes. In certain research projects or where the equivalence of a new acquisition device is being compared to an existing commercial device this difference in the location that the signals are acquired from may require duplicate testing with each device being connected to each electrode location. Alternately, the differences may have to be estimated from a single test and then separately analyzed to determine if the differences in the acquired signals represent a statistically significant difference. Neither approach is particularly appealing and may be affected by a variety of factors which must either be accounted for or ignored.

Another difficulty with current practice of electrode placement is that motion artifacts have long been a problem during the measurement of biopotentials, particularly in long-term electrocardiogram (ECG) monitoring of coronary care patients and in exercise (stress) ECG's. Motion artifacts can be defined as motion induced fluctuation of the electrical potential across the skin of the patient. Motion artifacts manifest themselves as electrical interference which is often superimposed on the desired physiological signal and minimizes the usefulness of the physiological signal for diagnostic and clinical purposes. Motion artifacts are generally caused by the movement of the patient relative to the electrode applied to the patient's skin, thereby disturbing the skin potential and creating extraneous readouts on the ECG monitor which either mask or cause a shift in the baseline of the desired physiological signal. In clinical and comparative studies, the existence of motion artifacts may introduce yet another variable which must be ignored or accounted for in the study results. Additionally, if one acquired signal is closer to the source of the motion artifact than the other acquired signal, the comparison of the two signals may required increased filtering of one signal or other special treatment which may affect the comparative analysis of the study results.

It is well known that light abrasion of the skin reduces the electrical potential and minimizes the impedance of the skin of the patient, thereby reducing motion artifacts and improving signal or trace quality of the physiological signal. Although there are many commercially available surface mounted electrodes for cardiac monitoring described in the literature, reliable signals or trace results from these electrodes in highly dependent on adequate skin preparation prior to application of the electrodes. Proper skin preparation is time consuming because typical stress electrocardiograms usually require between three and 12 electrodes and typically use about 10 electrodes and research and comparative studies may use double that amount. Skin preparation is normally necessary to remove the epidermal layer of the skin of the patient and is carried out in a variety of ways. The most common method of preparing the skin is to rub the patient's skin with a gritty material contained in a carrier or to rub the patient's skin with a rough surfaced material to which an antiseptic such as alcohol or other solvent is applied. Other approaches include chemical preparations or a variety of mechanical abrasion. After briskly rubbing the skin, the skin is dried and again rubbed with a dry cloth. If, after the electrodes are applied, a proper signal or trace is not obtained from one or more of the electrodes, the malfunctioning electrodes must be identified, removed and the skin must be prepared again. The electrodes are then reapplied to the skin of the patient, and this procedure is repeated until an adequate and accurate signal is received from each electrode. The effectiveness of the skin preparation is highly dependent on the technique used as well as the level of skill of the person preparing the skin. Predictably, the effectiveness of the skin preparation in this uncontrolled manner is highly variable between electrode locations as well as between patients and represents yet another variable which may affect the results of the research or comparative study.

U.S. Pat. Nos. 4,274,419 and 4,311,152 are owned by the assignee of the present invention and disclose a single surface mounted medical electrode suitable for recording physiological measurements in which the electrode is first applied to the patient, and then the skin of the patient is prepared. Such an approach markedly reduces the time consumed in the application of electrodes for recording physiological events. Also, more reliable, accurate and uniform signals are obtained since the amount and type of skin preparation for each electrode is generally uniform.

SUMMARY OF THE INVENTION

It is a primary object of this invention to provide a dual contact medical electrode which has the ability to receive the physiological signal from a single location for use with multiple acquisition devices.

It is another object of this invention to provide an electrode which receives the physiological signals from a common location on the patient and which performs skin preparation after application of the electrode to the desired location on the skin of the patient and before the recording of physiological events.

It is yet another object of this invention to provide a dual contact medical electrode which provides for the acquisition of ECGs from a single electrode having a pair of metal or radiolucent snap members thereon.

It is yet another object of this invention to provide a dual contact medical electrode having one or more acquisition members thereon to allow for the acquisition of ECG signals which have statistically insignificant differences therein.

A preferred form of the electrode of the present invention includes a rotatable conductive means as well as a pair of snap members thereon; although, it is not necessary to include rotatable conductive means thereon in order to practice the most basic form of the present invention. The electrode may also include a rotatable penetration member associated therewith for the abrasion of the epidermal layer of skin. Both the conductive members and penetration members of the present invention may be rotated after application of the electrode to the skin of the patient to prepare the skin and thereby minimize motion artifacts arising from skin potential variations and skin impedance. The preferred form of the electrode of the present invention is also preferably pre-gelled and disposable although non pre-gelled or reusable electrodes are believed to be within the scope of the present invention.

In the present invention, the conductive members of the electrode retain the epidermal penetrating members therein and are preferably provided with an electrolyte such as a gel material in a recess formed between the conductive member and the penetrating member of each electrode. The conductive means is secured for rotational movement relative to an adhesive coated sheet member which is used to adhere the electrode to the skin. When the electrode is pre-gelled, it may be provided with a removable cover for protecting the adhesive coated sheet member and the penetrating means having the electrolyte gel therein. In a preferred form of the present invention, the conductive member is a carbon based, silver plated center member, and the penetrating means is preferably a flexible screen-type member. The snap members are preferably spaced apart from each other and may be preferably connected to a common conductive member, although a plurality of conductive members may be used as long as they are spaced apart a relatively short and preferably predetermined distance from each other.

It is a further object of this invention to provide a surface mounted medical electrode having a pair of snap members operatively connected to one or more conductive members and being capable of a more uniform and consistent skin preparation between individual electrodes and patients.

It is a further object of the present invention to provide an electrode which minimizes the interference of motion artifacts and skin impedance with physiological signals by providing a reliable and consistent method of abrading the skin of a patient.

It is a further object of this invention to provide a surface mounted medical electrode having a rotatable abrasive member for abrading the skin after application of the electrode to the patient wherein the abrasive member is operatively interconnected with one or more of the conductive members.

Another object of this invention is to provide a surface mounted electrode which eliminates technique variability in skin preparation and signal acquisition, thereby minimizing motion artifact between electrodes and signal acquisition sites while decreasing the likelihood that the quality and comparability of the acquired signals will vary due to operator induced variables.

It is yet another object of the present invention to provide a dual connector surface mounted electrode which is inexpensive to manufacture and easy to assemble.

DESCRIPTION OF THE PREFERRED EMBODIMENTS

Figure 1:
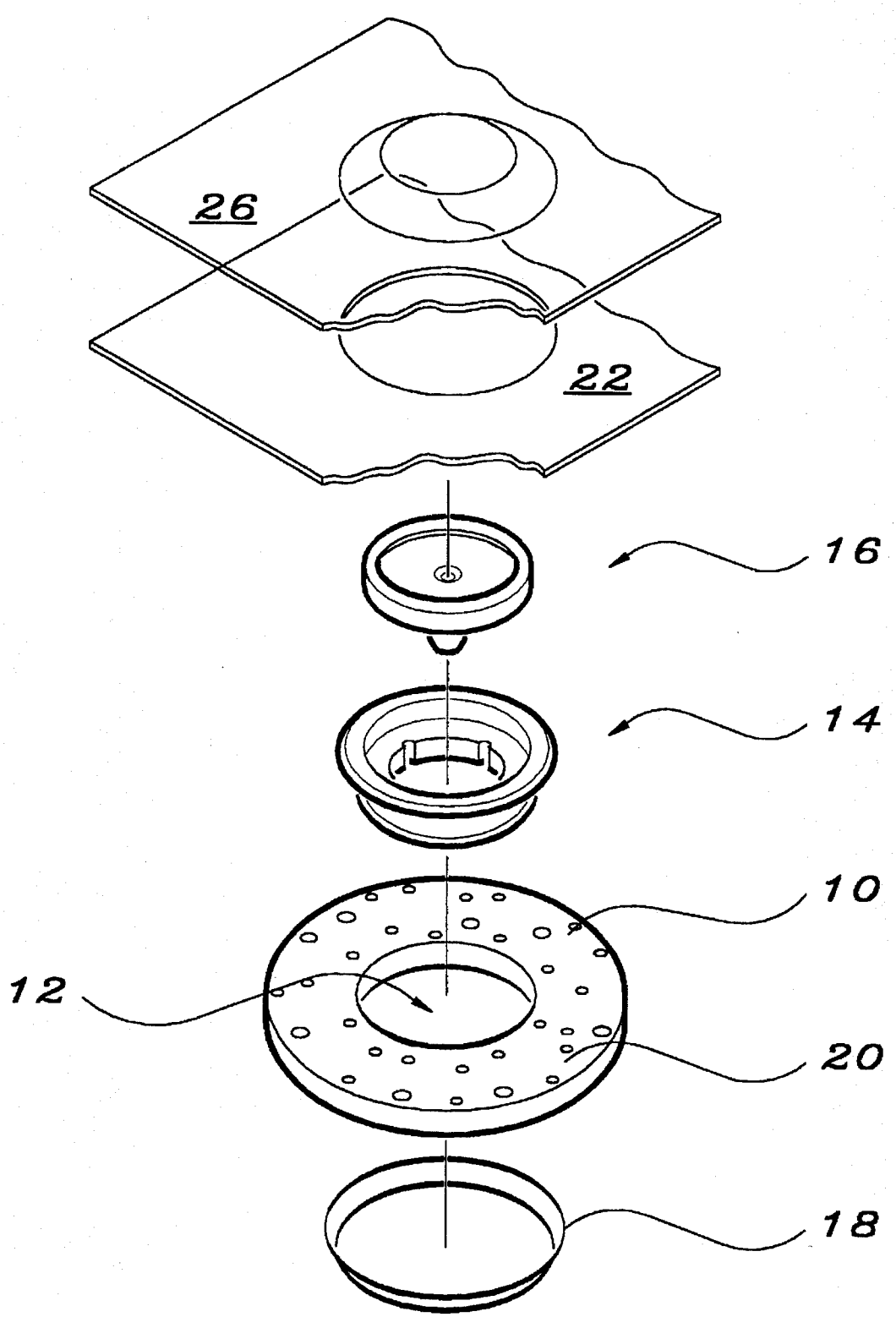
FIG. 1 is an exploded view of a prior art surface mounted medical electrode, illustrating the components which make up the electrode except for the abrasive electrolyte-containing member.

FIGS. 1–4 illustrate a surface mounted electrode and applicator gun 70 of the prior art which are more fully set forth in U.S. Pat. Nos. 4,274,419 and 4,311,152. These patents are commonly owned by the assignee of the present invention and are incorporated herein as if fully set forth below. The prior art electrodes of FIGS. 1–4 are described herein to provide a better understanding of the differences in structure and function of the prior art electrodes and the present invention. The prior art electrode shown in FIGS. 1–4 generally consists of a circular sheet member 10 having an annular cutout portion 12 in the center thereof into which a collar 14 is inserted. The collar 14 is shaped to hold an electrically conductive member 16 therein. A ring member 18 is further employed to clamp around the upper portion of the collar 14. The sheet member 10 is coated on one side with a skin adhesive layer 20. The adhesive is protected during storage with a protective cover 22. A spongy abrasive member 24 (see FIG. 2) is provided with an electrolyte gel thereon and is placed in contact with the conductive member 16. The abrasive member 24 is protected during storage with the protective cover 24.

The prior art collar 14 of FIGS. 1–4 has the general configuration of an inverted hat with a flat base surface 28 and a vertical wall surface 30 which is normal and integral with the flat base surface 28 and which terminates in a contoured flange 32. The flat base surface 28 has an annular opening 34 in the center thereof with a diameter less than the diameter of the inner wall 30. Around the annular opening 34, is a vertical wall 36 having slots 38 cut therein about every 90 degrees. The walls 30 and 36 extend above the plane of the base 28 leaving a channel 40 therebetween. The collar 14 is generally molded from a semi-flexible, nonconductive plastic material such as an acetate-based material, nylon, polyester, polyethylene or polypropylene. The wall 36 is made sufficiently thin so that it can be flexed under pressure. The diameter of the collar 14 is substantially greater than its height. The inner periphery of the wall 36 is provided with a ridge 42 which functions to retain the conductive member therein.

Figure 2A:
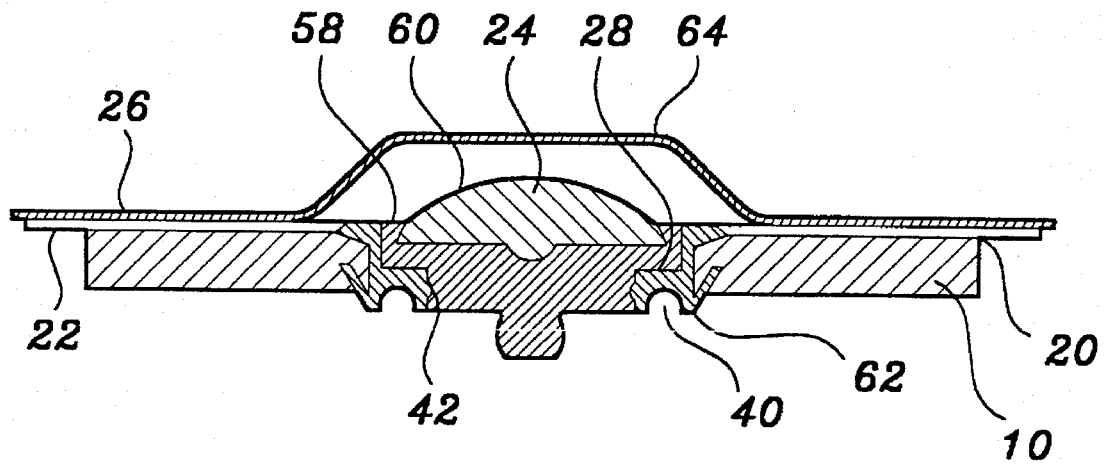
FIGS. 2A and 2B are cross-sectional views of the prior art electrode of FIG. 1.
Figure 2B:
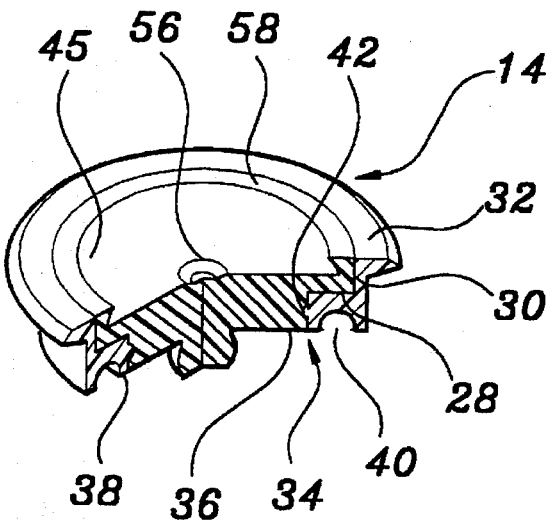
Figure 3:
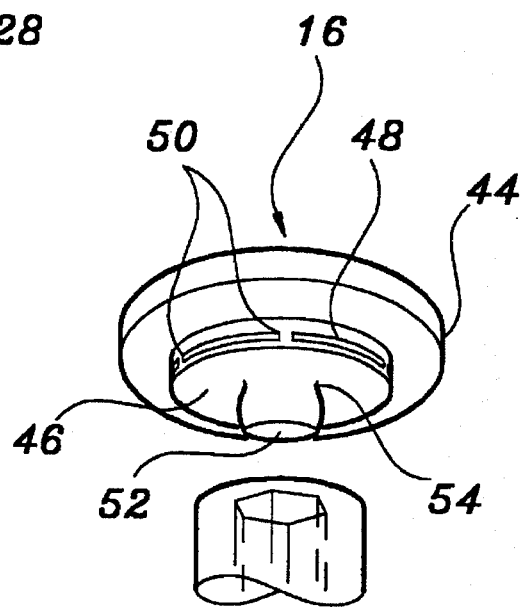
FIG. 3 is a perspective view of the projecting stud of the prior art conductive member and the coupler of the prior art applicator gun illustrating the manner in which the applicator gun is connected to the stud of the prior art electrode of FIG. 1 for rotation of the conductive member by the applicator gun.

The prior art electrically conductive member 16 of FIGS. 1-4 is adapted to be snapped into the collar 14. The electrically conductive member 16 may be manufactured from a synthetic resin impregnated with carbon from a suitable electrically conductive metal or metal containing material or other suitable electrically conductive material. As shown in FIGS. 2 and 3, the electrically conductive member 16 includes a lower portion 44 having a textured convex lower surface 45 and a thickness substantially equal to the depth of the cup formed by the flange 32, wall 30 and base 28 of the collar. Integral with the lower portion 44 is an upper portion 46 of reduced diameter relative to the lower portion. The upper portion 46 has a diameter equal to that of the annular opening 34 in the collar 14. The circumference of the upper portion has a slot 48 therein which is interrupted by detents 50 positioned normal to the slot 48. The slot 48 of the conductive member 16 receives the ridge 42 in the wall 36 of the collar 14 to prevent the conductive member from moving vertically within the collar. The detents 50 of the conductive member 16 engage in the slots 38 in the flexible wall 36 of the collar 14 to prevent the conductive member from being rotated except by the predetermined torque/force of the applicator gun 70. A downwardly extending stud 52 provided on the bottom of the conductive member 16 preferably includes a polygonal outer surface 54 so that the coupler of the applicator gun can be drivingly secured over the stud to rotate the conductive member 16.

Figure 4:
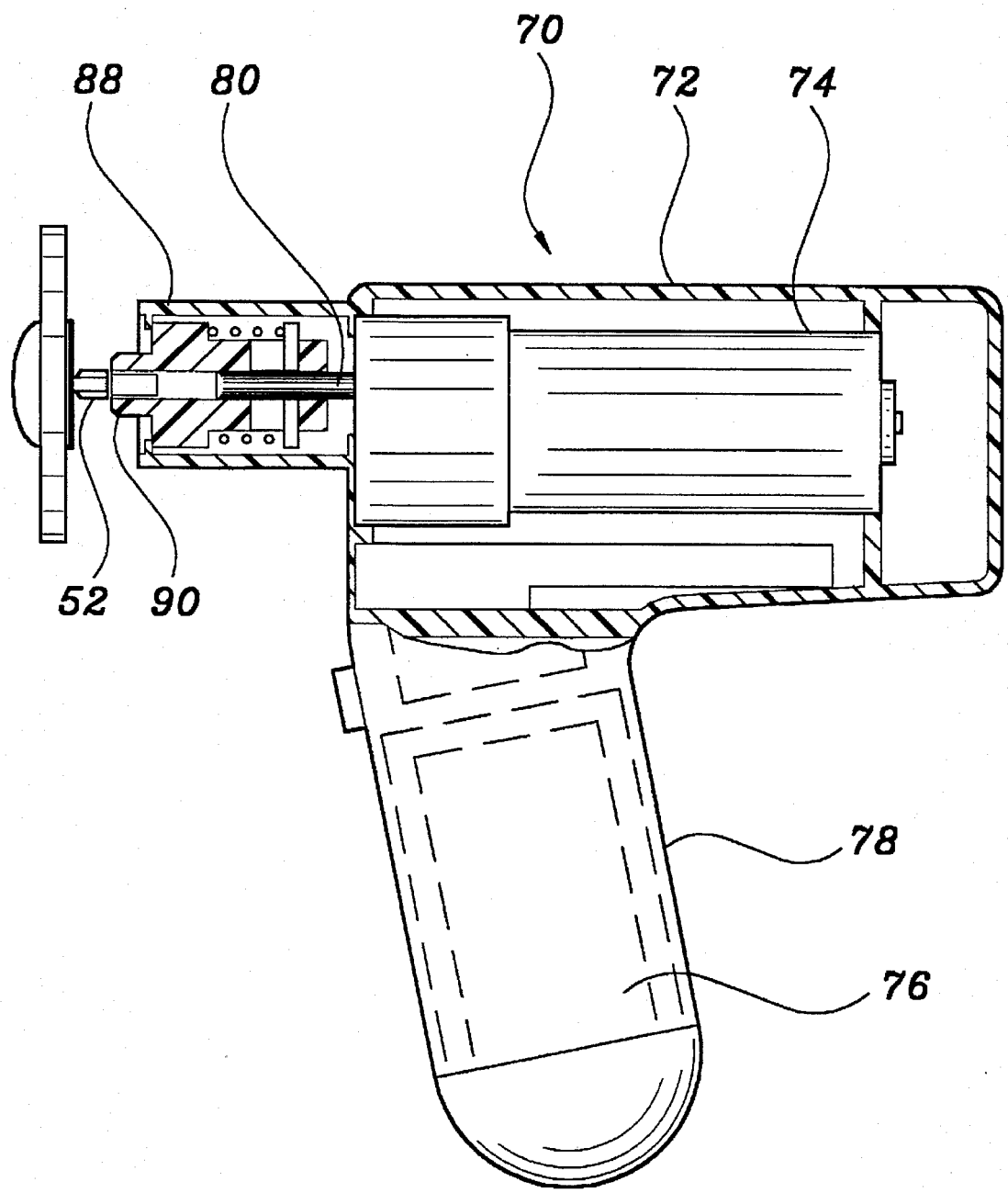
FIG. 4 is a schematic view of a prior art applicator gun used to drive the movable conductive element and abrasive member of the prior art electrode of FIG. 1 and the electrode of the present invention to perform skin preparation.

The prior art penetrating means for abrading or penetrating the epidermal layer of skin is a separate porous abrasive member 24 as illustrated in FIGS. 2A and 4. The abrasive member 24 is a generally fibrous pad incorporating abrasive fibers and having a convexly curved surface 60 and a diameter substantially the same as the diameter of the lower portion 44 of the conductive member 16. A flange 58 is folded against the edges of the abrasive member 24 to clamp the abrasive member 24 in the conductive member 16. The prior art abrasive member 24 is loaded with electrolyte gel so that when the electrode is applied to the skin, the electrolyte gel provides electrical contact between the skin and the conductive member 16.

The assembled collar 14, conductive member 16 and abrasive member 24 are snapped together and placed in the annular opening 12 of the adhesive coated sheet member 10. The adhesive coating 20 contacts the upper surface of the flange 32 of the collar 14 to secure the collar 14 in place relative to the sheet member. A snap ring 18 as shown in FIG. 1 is snapped over the wall 30 of the collar. The snap ring 18 is held in place by a ridge 62 extending around the outer terminating edge of the wall 30 of the collar 14.

FIGS. 3 and 4 generally illustrate the prior art applicator gun 70 which is used with the electrode described above as well as the present invention described below. The applicator gun 70 generally includes a housing 72 within which is mounted an electric motor 74 driven by AC or DC current from a suitable current source. The motor illustrated is driven by a rechargeable battery 76 held in place in a quickly disconnectable case 78 which also serves as the handle of the applicator. The lower end of the case includes recessed electrical contacts 79 for battery recharging. The motor has a shaft 80 to which a coupler 88 is attached. The coupler 88 includes a polygonal recess 90 thereon which is shaped to receive the specifically shaped stud 52 of the electrode therein.

FIGS. 5-11 are illustrative of the preferred forms of the present invention. The electrode 110 of the present invention is preferably a radiolucent member which consists generally of an electrically conductive center member 112 which is received in a circumferential housing 114. The housing 114 includes a flexible screen member 116 received therein on the side of the housing 114 opposite to the center member 112. As with the prior art electrode described above, the electrode 100 of the present invention may further include an adhesive coated sheet member 118 surrounding a retaining ring 150. The sheet member 118 is preferably formed of a cross linked polyethylene foam having an adhesive thereon to facilitate the attachment of the electrode 100 to the skin of the patient. Prior to use, the adhesive surface of the sheet member 118 is protected by a paper-like protective cover 120, and the surface of the electrode is further protected in a tray-like package (not shown) or by a further protective cover 121.

Figure 5:
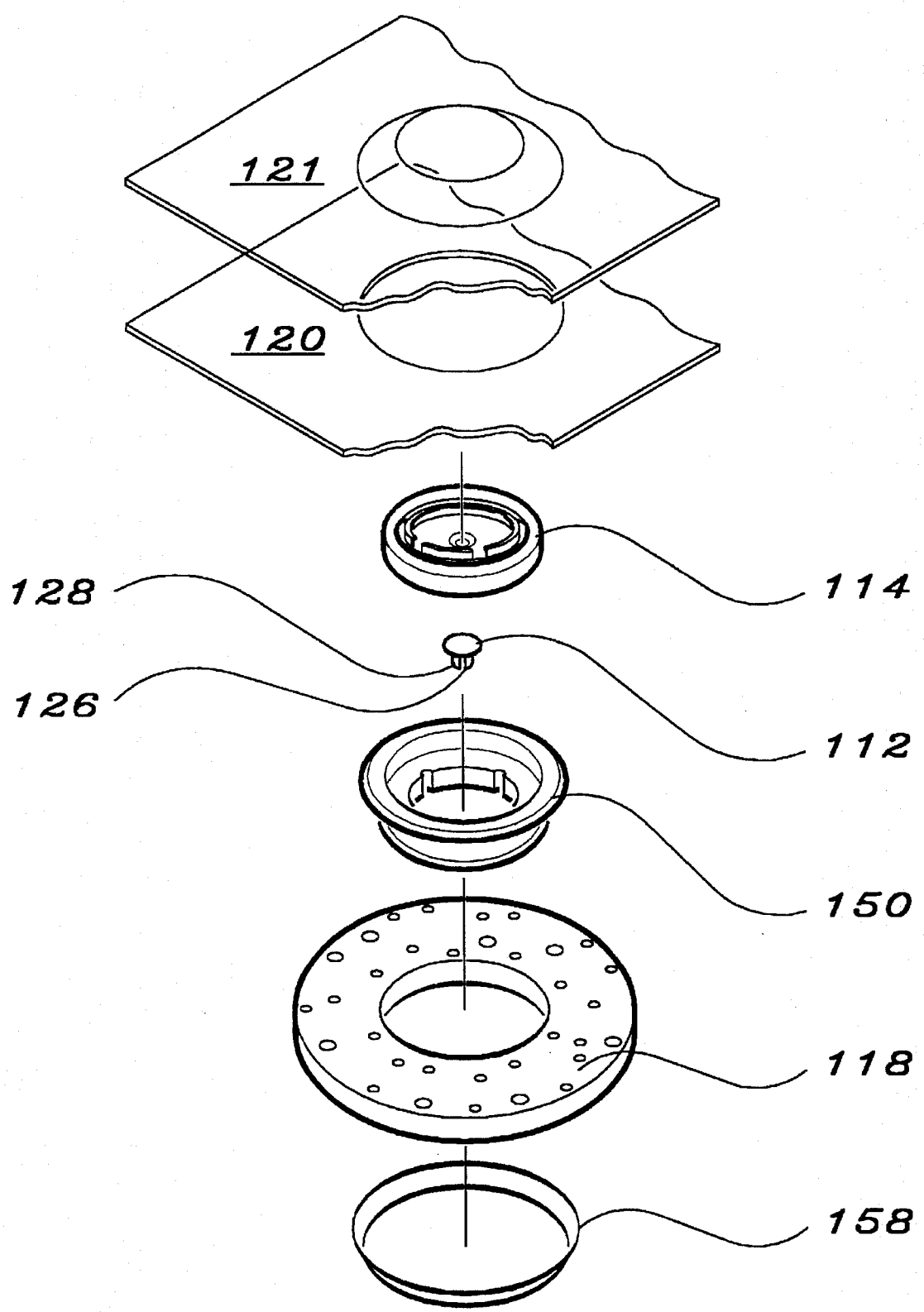
FIG. 5 is an exploded perspective view of a preferred form of the electrode of the present invention.
Figure 6:
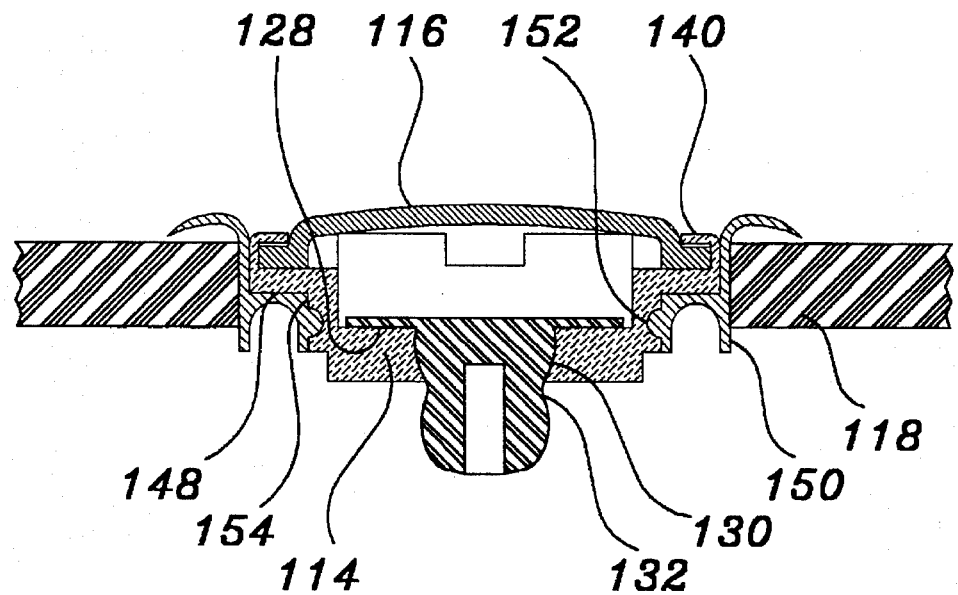
FIG. 6 is an elevated view of the bottom surface of the assembled electrode of the present invention shown in FIG. 5.

In the preferred form of the present invention, the center member 112 is preferably a plastic carbon member having a thin silver plated layer thereon which has been treated with silver chloride to enhance ion flow therethrough as well as to form a low impedance point of connection with the wires (not shown) of the electrode. Alternately, the center member may be formed of a metal or other material to provide the desired conduction of the physiological signal from the skin of the patient to the signal acquisition device As shown in FIGS. 5 and 6, the center member 112 of the present embodiment includes a generally flat first surface 122 which faces the skin of the patient in use. The center member 112 includes a circularly shaped outer circumference having a diameter which is greater than the diameter of the aperture 134 in the housing 114 as described below. As shown in FIG. 6, the second surface 124 of the center member 112 faces away from the skin of the patient in use and preferably includes a pair of post members 126 and 128 extending therefrom. The post members 126 and 128 preferably each include a tapered surface 129 thereon which extends from the second surface 124 of the center member 112. The tapered surface 129 of each post member 126 and 128 preferably includes a slight rib 130 thereon and decrease in circumference to form a snap area 132 on each of the post members 126 and 128. The snap areas are contacted and engaged by a snap type of electrode connector (not shown) to supply physiological signals which originate from the same location for use by a plurality of signal acquisition devices. The rib 130 is shaped to frictionally contact a portion of the housing 114 described below. Unlike the prior art post member 52 shown above in FIGS. 1-4, the post members 126 and 128 of the present invention are preferably not hexagonally or otherwise particularly shaped to receive reciprocal motion from the prior art applicator gun 70 (FIG. 4) thereon although the tip of the applicator gun may be readily modified to engage and rotate the pair of post members 126 and 128 as described above.

The circumferential housing 114 of the present embodiment is preferably formed of a rigid plastic or similar material. As shown in FIGS. 6, the housing 114 includes an aperture 134 extending therethrough and first and second surfaces 136 and 138 respectively. The aperture 134 is formed to frictionally receive the center member 112 therein. The first surface 136 of the housing 114 is best shown in FIG. 5. The first surface 136 includes an outer circumferential rib 140 which forms the outer periphery of the housing 114 and an inwardly positioned annular ring shaped surface 142 having a plurality of channels 144 formed therein. During assembly, the circumferential rib 140 is crimped or otherwise formed to retain the screen member 116 thereon as shown in FIG. 6. A recessed area 146 is also located inwardly of the annular surface 142 to surround the aperture 134 and receive the first and second surfaces 122 and 124 of the center member 112 therein.

The second surface 138 of the housing 114 preferably includes a generally flat contact surface 148 which is shaped to receive a portion of the retaining ring 150 thereagainst in a manner similar to the contact between the collar 14 and the conductive member 16 as shown in FIG. 2. The sidewall surface 154 of the housing 114 extends outwardly from the contact surface 148 and includes a circumferential recess 152 therein. The circumferential recess 152 is sized to frictionally receive a portion of the retaining ring 150 therein. As with the collar 14 shown in FIG. 2, the retaining ring 150 of the present invention extends between the outer surface of the housing 114 and the sheet member 118 to retain the housing 114, center member 112 and screen member 116 while allowing relative movement between the housing 114 and retaining ring 150. Additionally, a snap ring 158 is positioned between the outer surface of the retaining ring 150 and the sheet member 118 to prevent movement between the sheet member 118 and the retaining ring 154.

The screen member 116 of the present invention is preferably constructed of a flexible silicon carbide or other abrasive material. The screen member 116 is sized so that when the outer circumference of the screen member 116 is positioned generally inwardly from and adjacent to the crimped outer circumferential rib 140, the screen member 116 contacts the annular ring surface 142 of the housing 114 and is bowed slightly outwardly therefrom. This orientation is particularly useful to provide consistent abrasion of the skin of the patient because if the user of the applicator gun presses too hard during the preparation of the skin of the patient, the screen member 116 will preferably flex to decrease the abrasion of the skin.

The flexibility of the screen member 116 and the orientation of the screen member 116 with respect to the housing 114 and center member 112 may also be particularly important during the use of the electrode. The electrolyte gel (not shown) is preferably initially placed in the housing 114 to fill the space between the first surface 136 of the housing 114, the first surface 122 of the center member 112 and the screen member 116. When the electrode is applied to the skin of the patient, the sheet member 118 encircles the periphery of the housing 114 such that the electrolyte gel is trapped therein to provide for the electrical conduction of the physiological signal from the skin of the patient to the center member 112 and the signal acquisition device. During certain procedures such as ECG stress tests, the patient is exercising or otherwise moving around. This movement may cause the skin which is in contact with the various electrodes to stretch or contract according to the movements of the patient. During this movement, the skin may press against or move away from the prior art electrodes. This movement between the electrode and the skin of the patient may cause muscle artifact and may even break the signal between the patient and the signal acquisition device. During use of the electrode of the present embodiment, the electrolyte gel forms a gel column in the electrode which responds to the movement of the skin of the patient to ensure that the electrolyte gel maintains electrical contact between the skin of the patient and the center member 112. Although, the use of a gel form of the electrolyte is preferred, a solid or wet gel may also be used to maintain contact between the center member 112 and the skin of the patient. The area between the circumferential rib 140 and the annular surface 142 on the first surface 136 of the housing 114 functions basically as a reservoir area 160 for the electrolyte gel in the present embodiment. For example, if the skin of the patient presses against the slightly flexed or raised center of the mesh screen, the electrolyte gel is pushed back into the recess of the housing and is forced to flow to the outer periphery of the housing 114 through the channels 144 in the annular surface 142 to the reservoir area 160 of the housing 114 between the circumferential rib 140 and the annular surface 142. When the skin of the patient draws away from the electrode, the electrolyte gel is drawn from the reservoir area 160 of the housing 114 through the channels 144 and into the recessed area 146 to ensure that a continuous column of electrolyte gel extends between the skin of the patient and the center member 112.

Figure 7:
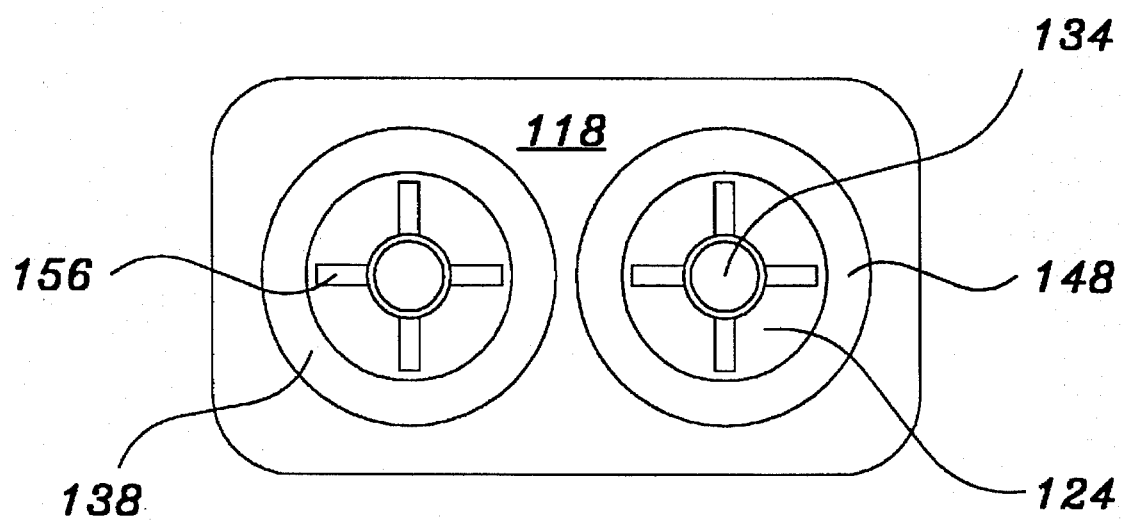
FIG. 7 is an elevated view of an alternate form of the electrode of the present invention.
Figure 8:
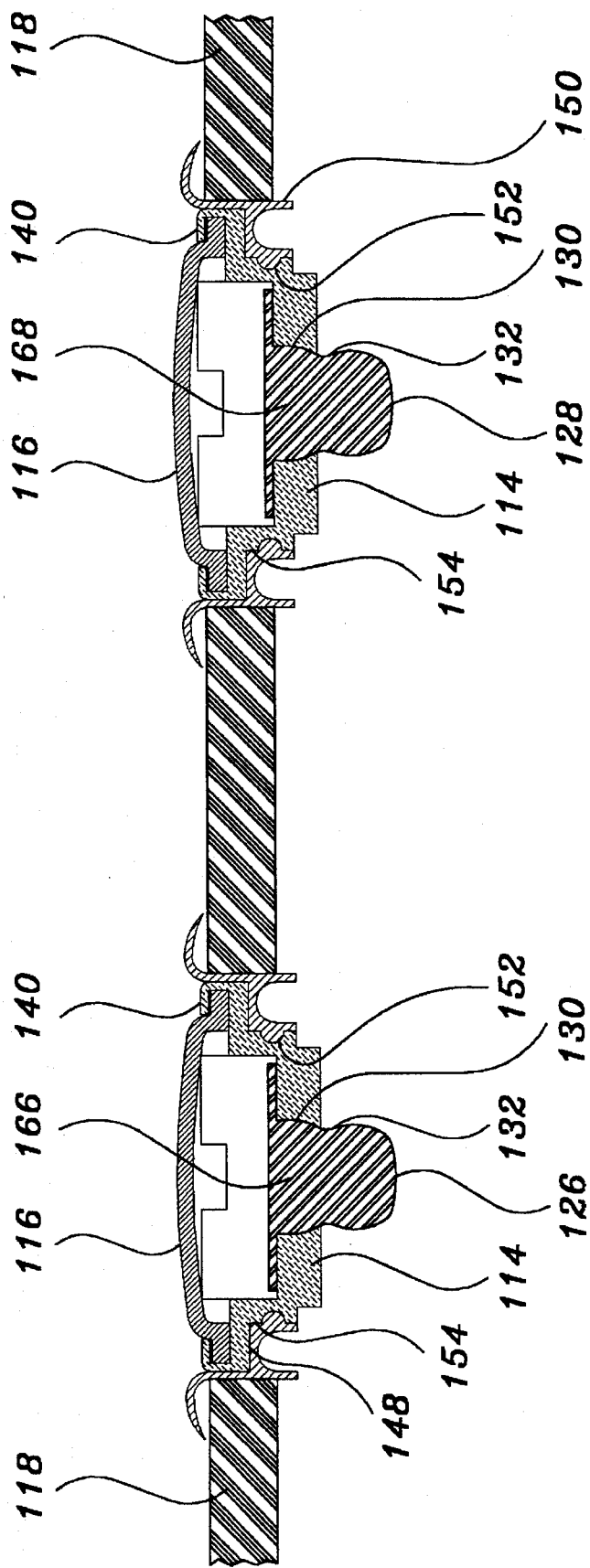
FIG. 8 is a cross sectional view of the electrode of the present invention shown in FIG. 7 taken generally along lines 8—8 of FIG. 7.

FIGS. 7 and 8 are illustrative of a further embodiment of the present invention wherein the pair of post members 126 and 128 are operatively connected to individual center members 166 and 168 rather than the common center member 112 as shown in FIGS. 5 and 6. In this embodiment, the electrode assembly includes a pair of electrodes each having center members, housings, snap rings and the other components described above, all of which are commonly connected to a single sheet member 118 which retains the electrodes in a fixed and spaced apart relationship with respect to each other so that research and comparative studies performed with this electrode assembly may have a variability of a known quantity between each of the acquisition sites to allow the researcher and/or study coordinator to eliminate the effect of the distance between the signal acquisition sites as a variable in the study. The electrode assembly of this embodiment operates generally in the same manner as the preferred embodiment; and, therefore, like numbers have been added to like members, and the features common to each embodiment are not separately repeated herein.

Figure 9:
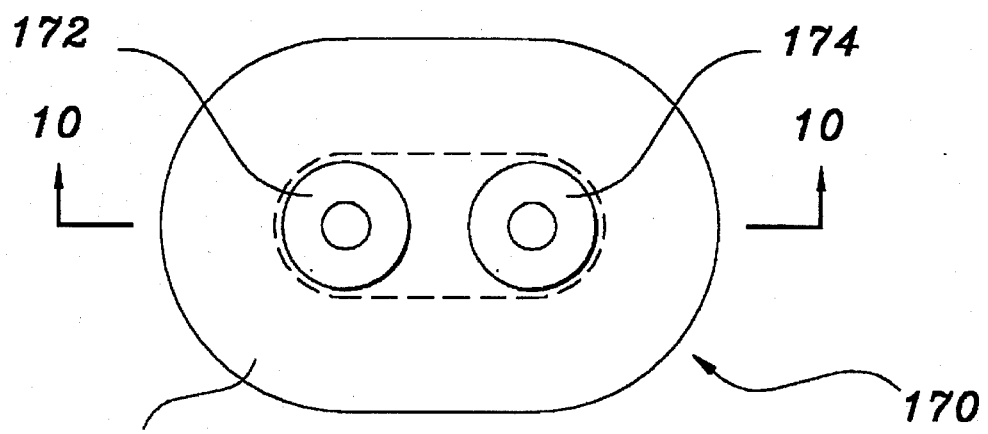
FIG. 9 is an elevated view of an alternate form of the electrode of the present invention.
Figure 10:
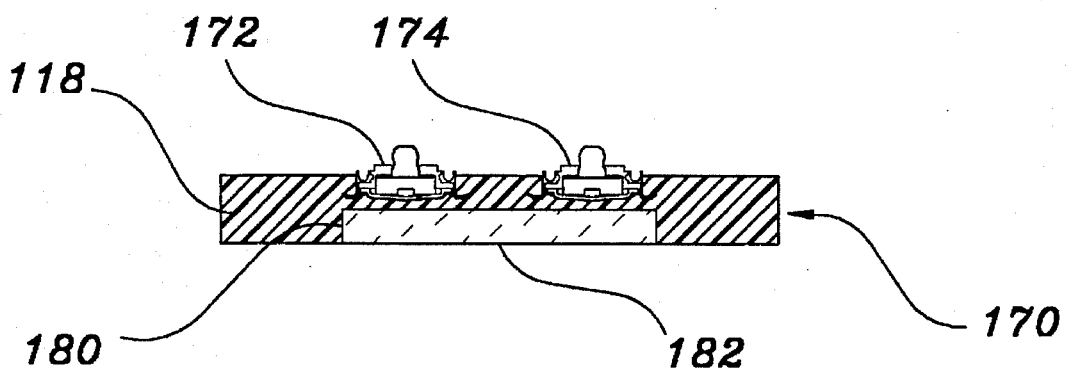
FIG. 10 is a cross sectional view of the alternate embodiment of the present invention shown in FIG. 9, taken generally along lines 10—10 of FIG. 9.
Figure 11:
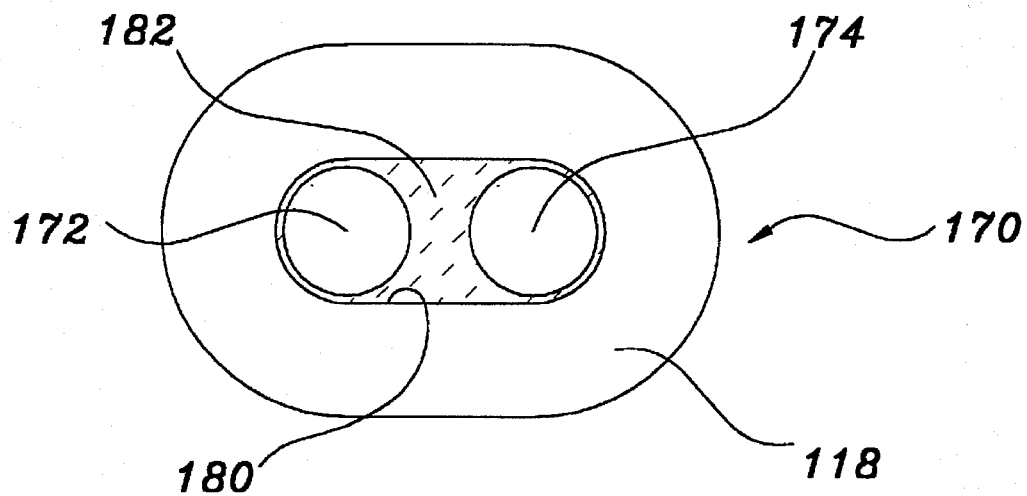
FIG. 11 is an elevated bottom view of the alternate embodiment shown in FIG. 9 with the electrolyte gel removed to show the center members.

FIGS. 9–11 are illustrative of a further variation of an alternate form of electrode assembly 170 of the present invention wherein the electrode assembly includes a pair of center members 172 and 174 each having their own post members thereon, 176 and 178, respectively. As shown in FIG. 9, The center members 172 and 174 are preferably oriented horizontally along the electrode assembly 170. As shown in FIG. 10, the center members 172 and 174 are in operative and conductive contact with a recess 180 on the surface of the electrode assembly 170 which contacts the skin of the patient in use. The electrode assembly 170 of this embodiment consists of the sheet member 118 with an adhesive on one surface thereof; the recess 180 which is shaped to receive a conductive material such as an electrolyte gel 182 therein and the center members 172 and 174 each having a post member 176 and 178 thereon. This embodiment is particularly adapted for use as a low cost electrode assembly 170 and includes the electrically conductive center members 172 and 174 operatively connected to a common centrally located recess area 180 which may be of nearly any desired shape. The center members 172 and 174 are preferably positioned on a relatively small sheet member 118 and are spaced apart from each other a relatively small distance so that the snap connectors (not shown) may be connected thereto while the physiological signals are received from a common recess area 180 via the electrolyte gel 182 so that the acquisition devices are provided with physiological signals from a common source on the skin of the patient.

The foregoing is intended to be illustrative of the currently preferred forms of the present invention which are defined by the following claims.

What is claimed is:

1. A medical electrode assembly for attachment to the skin of a patient and improving the quality of physiological signal detection in clinical, research or comparative studies, said electrode assembly comprising:
   at least one conductive member capable of receiving and conducting physiological signals for receipt by a plurality of acquisition devices;
   a plurality of post members operatively associated with said at least one conductive member to enable the simultaneous acquisition of physiological signals from said at least one conductive member to a plurality of physiological signal acquisition devices; and
   a sheet member associated with said at least one conductive member for securing the electrode assembly to the skin of the patient.

2. The electrode assembly of claim 1 wherein said at least one conductive member is movable relative to the sheet member.

3. The electrode assembly of claim 1 wherein said at least one conductive member is fixed relative to the sheet member.

4. The electrode assembly of claim 1 wherein said at least one conductive member is a radiolucent member.

5. The electrode assembly of claim 1 wherein said at least one conductive member is a metal member.

6. The electrode assembly of claim 1 wherein at least one conductive member includes said plurality of post members extending from a second surface thereof wherein said second surface is spaced apart from a first surface which is oriented to be positioned in operative physiological signal conducting contact with the skin of the patient.

7. The electrode assembly of claim 6 wherein said first surface of said at least one conductive member is in operative physiological signal conducting contact with an electrolyte gel.

8. The electrode assembly of claim 1 wherein the electrode assembly further includes at least one housing therein and wherein said at least one housing frictionally engages said at least one conductive member.

9. The electrode assembly of claim 1 wherein a recessed area is formed in said sheet member and a physiological signal transmitting material is located in said recessed area to be adapted for conductive contact with the skin of the patient.

10. The electrode assembly of claim 9 wherein said transmitting material is an electrolyte gel.

11. The electrode assembly of claim 1 including a plurality of conductive members thereon and including a post member operatively associated with each of said conductive members.

12. The electrode of claim 11 wherein said conductive members and said post members are positioned in a fixed and spaced apart relationship on said sheet member.

13. A medical electrode assembly which allows preparation of the skin of a patient to reduce motion artifacts after application of the electrode assembly to the skin of the patient while allowing the acquisition of physiological signals by a plurality of acquisition devices, said electrode assembly comprising:
   at least one electrically conductive member having a first surface facing the skin of a patient when the electrode assembly is adhered to the skin;
   a sheet member for holding said at least one electrically conductive member, said sheet member having an adhesive thereon for adhering the electrode assembly to the skin of the patient and for enabling the rotation of said at least one electrically conductive member relative to the skin of the patient;
   an abrasive member spaced apart from said at least one electrically conductive member;
   a plurality of post members in conductive contact with said at least one electrically conductive member for the simultaneous operative conduction of the physiological signals from the skin of the patient to a plurality of acquisition devices; and
   an electrolyte gel in operative contact with said at least one electrically conductive member and the skin of the patient when the electrode assembly is secured to the skin of the patient, said at least one electrically conductive member and said abrasive member being rotatable relative to the skin of the patient and said sheet member.

14. The electrode assembly of claim 13 wherein said abrasive member is a resilient screen shaped member with said electrolyte gel operatively interposed between said screen shaped member and said at least one electrically conductive member.

15. The electrode assembly of claim 13 wherein said electrode assembly includes a plurality of said conductive members and each of said conductive members is provided with a post member for operative connection to a signal acquisition device.

16. A disposable pre-gelled medical electrode assembly for use on the skin of a patient, said electrode assembly comprising:
   at least one electrically conductive member having a first surface facing the skin of the patient when the electrode is placed on the skin;
   a pair of post members on a second surface of said at least one conductive member for connection to a plurality of external signal acquisition devices for the simultaneous conduction of physiological signals from a patient therethrough;
   a flexible sheet member having an adhesive thereon for holding said at least one electrically conductive member in conductive contact with the skin of the patient.

17. The electrode assembly of claim 16 wherein said sheet member includes a recess therein and said at least one electrically conductive member is in conductive contact with said pair of post members.

* * * * *